United States Patent
Eicken et al.

(10) Patent No.: US 7,358,213 B2
(45) Date of Patent: Apr. 15, 2008

(54) FUNGICIDAL MIXTURES FROM BENZOPHENONES AND N-BIPHENYL NICOTINAMIDES

(75) Inventors: Karl Eicken, Wachenheim (DE); Ingo Rose, Mannheim (DE); Eberhard Ammermann, Heppenheim (DE); Reinhard Stierl, Mutterstadt (DE); Gisela Lorenz, Hambach (DE); Siegfried Strathmann, Limburgerhof (DE); Maria Scherer, Landau (DE); Klaus Schelberger, Gönnheim (DE); Egon Haden, Kleinniedesheim (DE); Manfred Hampel, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 737 days.

(21) Appl. No.: 10/466,165

(22) PCT Filed: Jan. 17, 2002

(86) PCT No.: PCT/EP02/00410

§ 371 (c)(1),
(2), (4) Date: Jul. 14, 2003

(87) PCT Pub. No.: WO02/056688

PCT Pub. Date: Jul. 25, 2002

(65) Prior Publication Data

US 2004/0077692 A1 Apr. 22, 2004

(30) Foreign Application Priority Data

Jan. 18, 2001 (DE) ................. 101 02 311

(51) Int. Cl.
*A01N 43/40* (2006.01)
(52) U.S. Cl. .................................... 504/130
(58) Field of Classification Search ................. 504/130
See application file for complete search history.

(56) References Cited

U.S. PATENT DOCUMENTS

| 5,330,995 | A |   | 7/1994 | Eicken et al. |  |
|---|---|---|---|---|---|
| 6,127,570 | A | * | 10/2000 | Curtze et al. | 560/140 |
| 6,169,056 | B1 | * | 1/2001 | Bayer et al. | 504/118 |
| 6,350,765 | B1 |   | 2/2002 | Schelberger et al. |  |
| 6,365,608 | B1 |   | 4/2002 | Schelberger et al. |  |
| 6,372,748 | B1 |   | 4/2002 | Schelberger et al. |  |

FOREIGN PATENT DOCUMENTS

| CA | 2312993 | 7/1999 |
|---|---|---|
| CA | 2312994 | 7/1999 |
| CA | 2313187 | 7/1999 |
| CA | 2313333 | 7/1999 |
| EP | 545 099 | 6/1993 |
| EP | 727 141 | 8/1996 |
| EP | 897 904 | 2/1999 |
| EP | 899 255 | 3/1999 |
| EP | 967 196 | 12/1999 |
| EP | 1 023 834 | 8/2000 |
| WO | 99/31951 | 7/1999 |
| WO | 99/31976 | 7/1999 |
| WO | 99/31979 | 7/1999 |
| WO | 99/31981 | 7/1999 |
| WO | 99/31983 | 7/1999 |
| WO | 99/31984 | 7/1999 |
| WO | 99/31985 | 7/1999 |

* cited by examiner

Primary Examiner—Alton Pryor
(74) Attorney, Agent, or Firm—Novak Druce + Quigg LLP

(57) ABSTRACT

Fungicidal mixtures, comprising
a) benzophenones of the formula I,

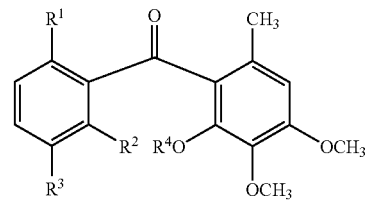

in which
$R^1$ is chlorine, methyl, methoxy, acetoxy, pivaloyloxy or hydroxyl;
$R^2$ is chlorine or methyl;
$R^3$ is hydrogen, halogen or methyl; and
$R^4$ is $C_1$-$C_6$-alkyl or benzyl, where the phenyl moiety of the benzyl radical may carry a halogen or methyl substituent, and
b) amide compounds of the formula II

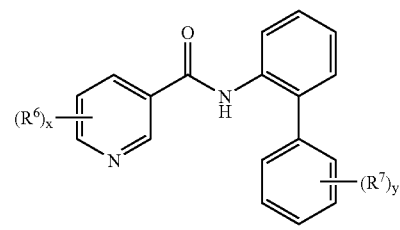

in which $R^6$ and $R^7$ are halogen nitro, cyano, alkyl, alkenyl, alkynyl, haloalkyl, haloalkenyl, haloalkynyl, alkoxy, haloalkoxy, alkylthio, haloalkylthio, alkylsulfinyl or alkylsulfonyl;
x is 1, 2, 3 or 4; and
y is 1, 2, 3, 4 or 5;
in a synergistically effective amount, methods for controlling harmful fungi using mixtures of the compounds I and II and compositions comprising them are described.

15 Claims, No Drawings

FUNGICIDAL MIXTURES FROM BENZOPHENONES AND N-BIPHENYL NICOTINAMIDES

The present invention relates to fungicidal mixtures, comprising
a) benzophenones of the formula I,

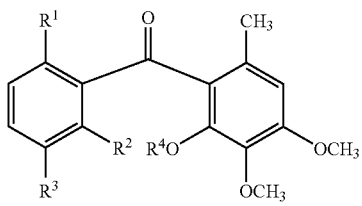

in which
$R^1$ is chlorine, methyl, methoxy, acetoxy, pivaloyloxy or hydroxyl;
$R^2$ is chlorine or methyl;
$R^3$ is hydrogen, halogen or methyl; and
$R^4$ is $C_1$-$C_6$-alkyl or benzyl, where the phenyl moiety of the benzyl radical may carry a halogen or methyl substituent, and
b) amide compounds of the formula II

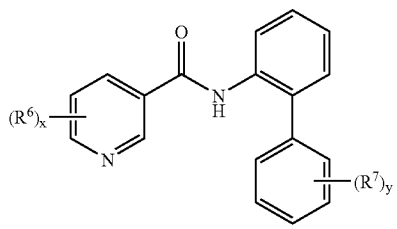

in which $R^6$ and $R^7$ are identical or different and are halogen, nitro, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl or $C_1$-$C_8$-alkylsulfonyl;
x is 1, 2, 3 or 4; and
y is 1, 2, 3, 4 or 5;
in a synergistically effective amount.

Moreover, the invention relates to methods for controlling harmful fungi using mixtures of compounds I and II and to compositions conditioned in two parts.

The compounds of the formula I, their preparation and their action against harmful fungi are known from the literature (EP-A 727 141; EP-A 897 904; EP-A 899 255; EP-A 967 196).

Mixtures of benzophenones of the formula I with other fungicidally active compounds are known from EP-A 1 023 834.

Also known are the amide compounds of the formula II, their preparation and their action against harmful fungi (EP-A 545 099).

It is an object of the present invention to provide mixtures which have an improved activity against harmful fungi combined with a reduced total amount of active compounds applied (synergistic mixtures), with a view to reducing the application rates and improving the activity spectrum of the known compounds I and II.

We have found that this object is achieved by the mixtures defined at the outset. Moreover, we have found that applying the compounds I and the compounds II simultaneously, i.e. together or separately, or applying the compounds I and the compounds II in succession provides better control of harmful fungi than is possible with the individual compounds alone.

The mixtures according to the invention act synergistically and are therefore particularly suitable for controlling harmful fungi and in particular powdery mildew fungi in cereals, vegetables, fruit, ornamental plants and grapevines.

The following compounds of the formula I are preferred mixing components, where the individual preferences apply on their own and in combination.

Preference is given to compounds I in which $R^1$ is chlorine, methoxy, acetoxy or hydroxyl, and particular preference is given to compounds in which $R^1$ is methoxy, acetoxy or hydroxyl. Very particular preference is given to compounds in which $R^1$ is methoxy.

Mixtures comprising compounds I in which $R^2$ is chlorine or methyl are mixtures according to the invention. Preference is given to compounds I in which $R^2$ is methyl.

Moreover, preference is given to compounds I in which $R^3$ is hydrogen, methyl, chlorine or bromine, particularly preferably hydrogen, chlorine or bromine.

In addition, preference is given to compounds I in which $R^4$ is $C_1$-$C_4$-alkyl or benzyl, where the phenyl moiety of the benzyl radical may carry a halogen or methyl substituent. Particular preference is given to compounds of the formula I in which $R^4$ is $C_1$-$C_4$-alkyl, preferably methyl.

Furthermore, preference is given to compounds of the formula I in which the substituents $R^1$, $R^2$, $R^3$ and $R^4$ are as defined below:
$R^1$ is methoxy, acetoxy or hydroxyl;
$R^2$ is methyl;
$R^3$ is hydrogen, chlorine or bromine; and
$R^4$ is $C_1$-$C_4$-alkyl.

In addition, particular preference is given to compound [sic] of the formula I in which the substituents have the meanings given in the table below:

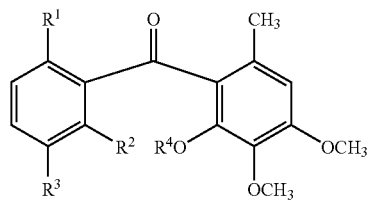

| No. | $R^1$ | $R^2$ | $R^3$ | $R^4$ |
|---|---|---|---|---|
| I-1 | methoxy | Cl | H | methyl |
| I-2 | methoxy | Cl | methyl | methyl |
| I-3 | methoxy | Cl | H | n-propyl |
| I-4 | methoxy | Cl | H | n-butyl |
| I-5 | methoxy | Cl | H | benzyl |
| I-6 | methoxy | Cl | H | 2-fluorobenzyl |
| I-7 | methoxy | Cl | H | 3-fluorobenzyl |
| I-8 | methoxy | Cl | H | 4-fluorophenyl |
| I-9 | methoxy | Cl | H | 2-methylphenyl |
| I-10 | methoxy | Cl | H | 3-methylphenyl |
| I-11 | methoxy | Cl | H | 4-methylphenyl |

-continued

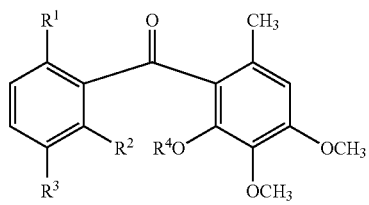

I

| No. | R¹ | R² | R³ | R⁴ |
|---|---|---|---|---|
| I-12 | methoxy | Cl | Br | methyl |
| I-13 | methoxy | Cl | Br | n-propyl |
| I-14 | methoxy | Cl | Br | n-butyl |
| I-15 | methoxy | Cl | Br | benzyl |
| I-16 | methoxy | Cl | Br | 2-fluorobenzyl |
| I-17 | methoxy | methyl | H | methyl |
| I-18 | methoxy | methyl | Cl | methyl |
| I-19 | methoxy | methyl | H | n-propyl |
| I-20 | methoxy | methyl | H | n-butyl |
| I-21 | methoxy | methyl | H | benzyl |
| I-22 | methoxy | methyl | H | 2-fluorobenzyl |
| I-23 | methoxy | methyl | H | 3-fluorobenzyl |
| I-24 | methoxy | methyl | H | 4-fluorophenyl |
| I-25 | methoxy | methyl | H | 2-methylphenyl |
| I-26 | methoxy | methyl | H | 3-methylphenyl |
| I-27 | methoxy | methyl | H | 4-methylphenyl |
| I-28 | methoxy | methyl | Br | methyl |
| I-29 | methoxy | methyl | Br | n-propyl |
| I-30 | methoxy | methyl | Br | n-butyl |
| I-31 | methoxy | methyl | Br | benzyl |
| I-32 | methoxy | methyl | Br | 2-fluorobenzyl |
| I-33 | acetoxy | methyl | H | methyl |
| I-34 | acetoxy | methyl | Cl | methyl |
| I-35 | acetoxy | methyl | Br | methyl |
| I-36 | hydroxy | methyl | H | methyl |
| I-37 | hydroxy | methyl | Cl | methyl |
| I-38 | hydroxy | methyl | Br | methyl |
| I-39 | pivaloyloxy | methyl | H | methyl |
| I-40 | pivaloyloxy | methyl | Cl | methyl |
| I-41 | pivaloyloxy | methyl | Br | methyl |
| I-42 | Cl | Cl | H | methyl |
| I-43 | Cl | Cl | H | n-propyl |
| I-44 | Cl | Cl | H | n-butyl |
| I-45 | Cl | Cl | H | benzyl |
| I-46 | Cl | Cl | H | 2-fluorobenzyl |
| I-47 | Cl | Cl | H | 3-fluorobenzyl |
| I-48 | Cl | Cl | H | 4-fluorophenyl |
| I-49 | Cl | Cl | H | 2-methylphenyl |
| I-50 | Cl | Cl | H | 3-methylphenyl |
| I-51 | Cl | Cl | H | 4-methylphenyl |
| I-52 | Cl | Cl | Br | methyl |
| I-53 | Cl | Cl | Br | n-propyl |
| I-54 | Cl | Cl | Br | n-butyl |
| I-55 | Cl | Cl | Br | benzyl |
| I-56 | Cl | Cl | Br | 2-fluorobenzyl |
| I-57 | methyl | methyl | H | methyl |
| I-58 | methyl | methyl | H | n-propyl |
| I-59 | methyl | methyl | H | n-butyl |
| I-60 | methyl | methyl | H | benzyl |
| I-61 | methyl | methyl | H | 2-fluorobenzyl |
| I-62 | methyl | methyl | H | 3-fluorobenzyl |
| I-63 | methyl | methyl | H | 4-fluorophenyl |
| I-64 | methyl | methyl | H | 2-methylphenyl |
| I-65 | methyl | methyl | H | 3-methylphenyl |
| I-66 | methyl | methyl | H | 4-methylphenyl |
| I-67 | methyl | methyl | Br | methyl |
| I-68 | methyl | methyl | Br | n-propyl |
| I-69 | methyl | methyl | Br | n-butyl |
| I-70 | methyl | methyl | Br | benzyl |
| I-71 | methyl | methyl | Br | 2-fluorobenzyl |

Suitable mixing components b) are the following amide compounds of the formula II

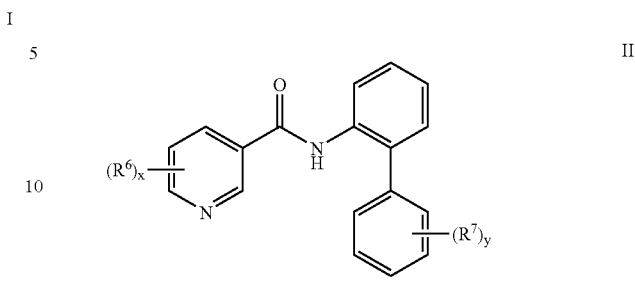

II in which $R^6$ and $R^7$ are identical or different and are halogen, nitro, cyano, $C_1$-$C_8$-alkyl, $C_2$-$C_8$-alkenyl, $C_2$-$C_8$-alkynyl, $C_1$-$C_8$-haloalkyl, $C_2$-$C_8$-haloalkenyl, $C_2$-$C_8$-haloalkynyl, $C_1$-$C_8$-alkoxy, $C_1$-$C_8$-haloalkoxy, $C_1$-$C_8$-alkylthio, $C_1$-$C_8$-haloalkylthio, $C_1$-$C_8$-alkylsulfinyl or $C_1$-$C_8$-alkylsulfonyl;

x is 1, 2, 3 or 4; and y is 1, 2, 3, 4 or 5.

Particularly suitable are compounds II in which $R^6$ is located in the 2-position of the pyridine ring and $R^7$ is located in the 4-position of the terminal benzene ring (formula II.1):

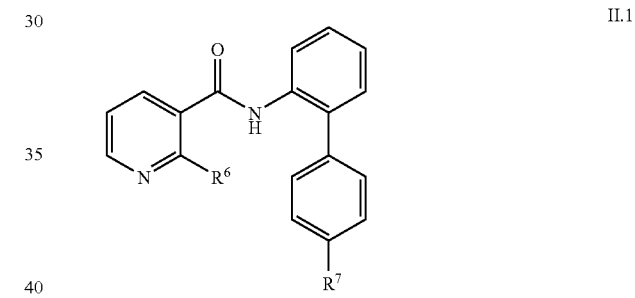

II.1

Particular preference is given to compounds of the formula II.1, in which the combination of the substituents corresponds in each case to one row of the table below:

| No. | R⁶ | R⁷ |
|---|---|---|
| II-1 | F | F |
| II-2 | F | Cl |
| II-3 | F | Br |
| II-4 | Cl | F |
| II-5 | Cl | Cl |
| II-6 | Cl | Br |
| II-7 | CF₃ | F |
| II-8 | CF₃ | Cl |
| II-9 | CF₃ | Br |
| II-10 | CF₂H | F |
| II-11 | CF₂H | Cl |
| II-12 | CF₂H | Br |
| II-13 | CH₃ | F |
| II-14 | CH₃ | Cl |
| II-15 | CH₃ | Br |
| II-16 | OCH₃ | F |
| II-17 | OCH₃ | Cl |
| II-18 | OCH₃ | Br |
| II-19 | SCH₃ | F |
| II-20 | SCH₃ | Cl |
| II-21 | SCH₃ | Br |

-continued

| No. | $R^6$ | $R^7$ |
|---|---|---|
| II-22 | $S(O)CH_3$ | F |
| II-23 | $S(O)CH_3$ | Cl |
| II-24 | $S(O)CH_3$ | Br |
| II-25 | $SO_2CH_3$ | F |
| II-26 | $SO_2CH_3$ | Cl |
| II-27 | $SO_2CH_3$ | Br |

Particular preference is given to the compounds II.1 in which $R^6$ is $CF_3$ or halogen and $R^7$ is halogen.

Preference is given to fungicidal mixtures which comprise, as component a), one of the compounds: I-33, I-35, I-42, I-44, I-46, I-60, or preferably I-18, I-28, I-37, and, as component b), one of the compounds: II-7, II-8 or, preferably, II-4 or II-5.

Owing to the basic character of their nitrogen atoms, the compounds II are capable of forming salts or adducts with inorganic or organic acids or with metal ions.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid, and alkanoic acids, such as acetic acid, trifluoroacetic acid, trichloroacetic acid and propionic acid, and also glycolic acid, lactic acid, succinic acid, citric acid, benzoic acid, cinnamic acid, oxalic acid, p-toluenesulfonic acid, salicylic acid, p-aminosalicylic acid, 2-phenoxybenzoic acid or 2-acetoxybenzoic acid.

Suitable metal ions are, in particular, the ions of the elements of the first to eighth transition group, in particular chromium, manganese, iron, cobalt, nickel, copper, zinc, and additionally those of the second main group, in particular calcium and magnesium, and of the third and fourth main group, in particular aluminum, tin and lead. If appropriate, the metals can exist in the various valencies which they can assume.

When preparing the mixtures, it is preferred to employ the pure active compounds I and II, to which further active compounds against harmful fungi or other pests, such as insects, arachnids or nematodes, or else herbicidal or growth-regulating active compounds or fertilizers can be admixed.

The mixtures of the compounds I and II, or the compounds I and II used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed also as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudocercosporella* species in hops and cucumbers, Alternaria species in vegetables and fruit, *Mycosphaerella* species in bananas and *Fusarium* and *Verticillium* species.

They can furthermore be employed in the protection of materials (for example the protection of wood), for example against *Paecilomyces variotii*.

The compounds I and II can be applied simultaneously, that is either together or separately, or successively, the sequence, in the case of separate application, generally not having any effect on the result of the control measures.

The compounds I and II are usually applied in a weight ratio of from 20:1 to 1:20, in particular from 10:1 to 1:10, preferably from 5:1 to 1:5.

Depending on the kind of effect desired, the application rates of the mixtures according to the invention are, in particular in agricultural crop areas, from 0.01 to 8 kg/ha, preferably 0.1 to 5 kg/ha, in particular 0.5 to 3.0 kg/ha.

The application rates of the compounds I are from 0.005 to 3.0 kg/ha, preferably 0.02 to 2.0 kg/ha, in particular 0.04 to 1.0 kg/ha.

Correspondingly, in the case of the compounds II, the application rates are from 0.005 to 5 kg/ha, preferably 0.08 to 3.0 kg/ha, in particular 0.06 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention or the compounds I and II can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by adding solvents and/or carriers. The formulations are usually admixed with inert additives, such as emulsifiers or dispersants.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90%.by weight, of one of the compounds I or II or of the mixture of the compounds I and II. The active compounds are employed in a purity of from 90% to 100%, preferably 95% to 100% (according to NMR spectrum or HPLC).

The compounds I or II, the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLE

The synergistic activity of the mixtures according to the invention was demonstrated by the following experiments:

The active compounds, separately or together, were formulated as a 10% emulsion in a mixture of 70% by weight of cyclohexanone, 20% by weight of Nekanil® LN (lutensol® AP6, wetting agent having emulsifying and dispersing action based on ethoxylated alkylphenols), and 10% by weight of Emulphor® EL Emulan® EL, emulsifier based on ethoxylated fatty alcohols), and diluted with water to the desired concentration.

Evaluation was carried out by determining the infected leaf areas in percent. These percentages were converted into efficacies. The efficacy (W) was calculated as follows using Abbot's formula:

$W = (1-\alpha) \cdot 100/\beta$

α corresponds to the fungal infection of the treated plants in % and
β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R.S. Colby, Weeds 15, 20-22 (1967)] and compared with the observed efficacies.

Colby's formula: $E = x + y - x \cdot y / 100$

E expected efficacy, expressed in % of the untreated control, when using the mixture of the active compounds A and B at the concentrations a and b
x efficacy, expressed in % of the untreated control, when using active compound A at a concentration a
y efficacy, expressed in % of the untreated control, when using active compound B at a concentration b.

Use Example 1: Protective activity against mildew of cucumbers caused by *Sphaerotheca fuliginea*

Leaves of cucumber seedlings of the cultivar "Chinesische Schlange" which had been grown in pots were, at the cotyledon stage, sprayed to runoff point with an aqueous preparation of active compound which had been prepared from a stock solution comprising 10% of active compound, 85% of cyclohexanone and 5% of emulsifier. 20 hours after the spray coating had dried on, the plants were inoculated with an aqueous spore suspension of mildew of cucumbers (*Sphaerotheca fuliginea*). The plants were then cultivated in a greenhouse at temperatures between 20 and 24° C. and at 60 to 80% relative atmospheric humidity for 7 days. The extent of the development of the mildew was then determined visually in % infection of the cotyledon area.

The visually determined values for the percentage of infected leaf areas were converted into efficacies as % of the untreated control. An efficacy of 0 means the same degree of infection as in the untreated control, an efficacy of 100 means 0% infection. The expected efficacies for combinations of active compounds were determined using Colby's formula (Colby, S.R. (Calculating synergistic and antagonistic responses of herbicide Combinations" [sic], Weeds, 15, p. 20-22, 1967) and compared to the observed efficacies.

TABLE A

| Active compound | Concentration of active compound in the spray liquor in ppm | Efficacy in % of the untreated control |
| --- | --- | --- |
| Control (untreated) | (83% infection) | 0 |
| Compound I-28 | 0.125 | 52 |
| Compound I-37 | 0.5 | 27 |
|  | 0.25 | 3 |
|  | 0.125 | 3 |
| Compound II-5 | 0.5 | 70 |
|  | 0.25 | 52 |
|  | 0.125 | 40 |

TABLE B

| Combinations according to the invention | Observed efficacy | Calculated efficacy*) |
| --- | --- | --- |
| Compound I-28 + compound II-5 0.125 + 0.25 ppm mixture 1:2 | 100 | 77 |
| Compound I-37 + compound II-5 0.25 + 0.5 ppm mixture 1:2 | 94 | 71 |
| Compound I-37 + compound II-5 0.125 + 0.25 ppm mixture 1:2 | 100 | 53 |
| Compound I-37 + Compound II-5 0.5 + 0.25 ppm mixture 2:1 | 94 | 65 |
| Compound I-37 + compound II-5 0.25 + 0.125 ppm mixture 2:1 | 88 | 42 |

*)calculated using Colby's formula

The test results show that in all mixing ratios the observed efficacy is higher than the efficacy which had been calculated beforehand using Colby's formula (from Synerg 166A.XLS).

We claim:
1. A fungicidal composition, comprising
a) benzophenones of the formula I,

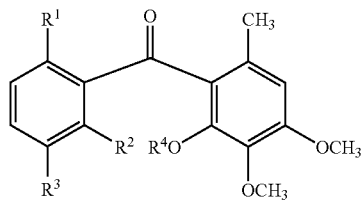

I in which
R¹ is methyl, or methoxy;
R² is chlorine or methyl;
R³ is hydrogen, halogen or methyl; and
R⁴ is $C_1$-$C_6$-alkyl, and
b) amide compounds of the formula II

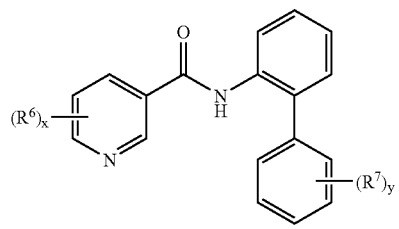

II in which R⁶ and R⁷ are identical or different and are halogen;
x is 1, 2, 3 or 4; and
y is 1, 2, 3, 4 or 5;
in a synergistically effective amount.

2. A fungicidal composition as claimed in claim 1, wherein
R¹ is methoxy;
R² is methyl;
R³ is hydrogen, chlorine or bromine; and
R⁴ is $C_1$-$C_4$-alkyl.

3. A fungicidal composition as claimed in claim 1, where the mixing components b) used are compounds of the formula II.1

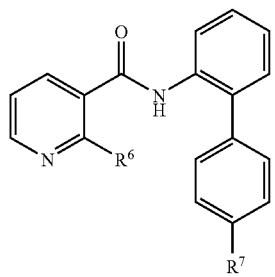

II.1 in which R⁶ is halogen and R⁷ is halogen.

4. A fungicidal composition as claimed in claim 1, wherein the weight ratio of the benzophenones I to the amide compounds of the formula II is from 20:1 to 1:20.

5. A method for controlling harmful fungi, which comprises treating the harmful fungi, their habitat or the plants, seeds, soils, areas, materials or spaces to be kept free from them with an effective amount of the fungicidal composition defined in claim 1.

6. A method as claimed in claim 5, wherein benzophenones of the formula I and amide compounds of the formula II are applied simultaneously, that is either together or separately, or successively.

7. A method as claimed in claim 5, wherein the benzophenones of the formula I are applied in an amount of from 0.02 to 2.0 kg/ha.

8. A method as claimed in any of claims 5, wherein the amide compounds of the formula II are applied in an amount of from 0.08 to 3.0 kg/ha.

9. A fungicidal composition as claimed in claim 1, which is conditioned in two parts, one part comprising benzophenones of the formula I in a solid or liquid carrier and the other part comprising amide compounds of the formula II in a solid or liquid carrier.

10. A fungicidal composition as claimed in claim 1, wherein R¹ is methoxy.

11. A fungicidal composition as claimed in claim 1, wherein R² is methyl.

12. A fungicidal composition as claimed in claim 1, wherein R⁴ is $C_1$-$C_4$-alkyl.

13. A fungicidal composition as claimed in claim 1, wherein
R¹ is methoxy,
R² is methyl,
R³ is bromine, and
R⁴ is methyl.

14. A fungicidal composition, comprising
a) benzophenones of the formula I,

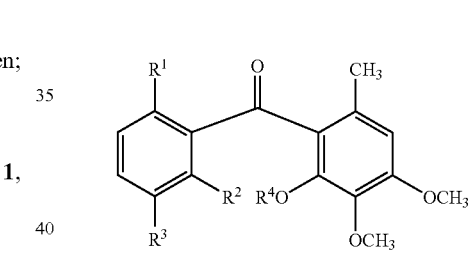

I in which
R¹ is methyl, or methoxy;
R² is methyl;
R³ is halogen; and
R⁴ is $C_1$-$C_6$-alkyl; and
c) amide compounds of the formula II

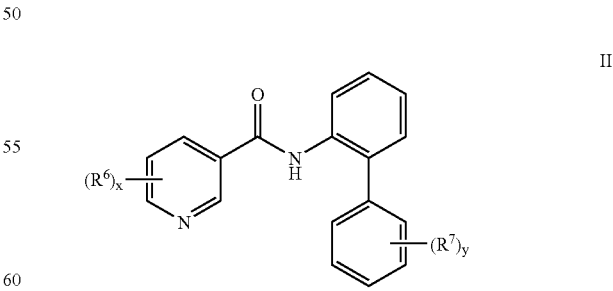

II in which R⁶ and R⁷ are identical or different and are halogen;
x is 1, 2, 3 or 4; and
y is 1, 2, 3, 4 or 5;
in a synergistically effective amount.

15. A fungicidal composition, comprising
a) benzophenones of the formula I,
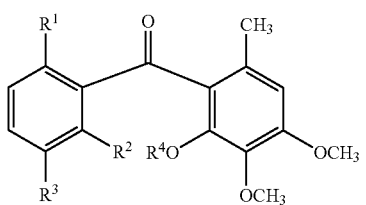
in which
R¹ is methoxy,
R² is methyl,
R³ is bromine, and
R⁴ is methyl.
d) amide compounds of the formula II.1
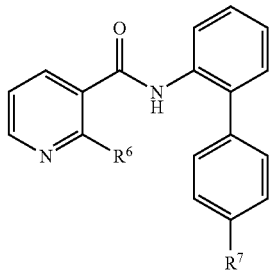
in which $R^6$ and $R^7$ are identical or different and are halogen;
in a synergistically effective amount.
* * * * *